United States Patent [19]

Kondo et al.

[11] Patent Number: 4,816,390

[45] Date of Patent: Mar. 28, 1989

[54] IMMUNOCHEMICAL ASSAY OF CARCINOEMBRYONIC ANTIGEN AND REAGENT THEREFOR

[75] Inventors: Koichi Kondo, Osaka; Nobuhiro Suzuki, Suita, both of Japan

[73] Assignee: Takeda Chemical Industries, Ltd., Osaka, Japan

[21] Appl. No.: 721,901

[22] Filed: Apr. 10, 1985

[30] Foreign Application Priority Data

Apr. 10, 1984 [JP] Japan .................................. 59-72427
Apr. 10, 1984 [JP] Japan .................................. 59-72428
Apr. 10, 1984 [JP] Japan .................................. 59-72429

[51] Int. Cl.$^4$ ............................................ G01N 33/53
[52] U.S. Cl. .......................................... 435/7; 435/28; 435/810; 436/518; 436/813
[58] Field of Search ............... 436/532, 813, 543, 548, 436/518; 435/7, 28, 68, 172.2, 188, 240, 810, 948; 530/389; 424/88; 935/102, 110

[56] References Cited

U.S. PATENT DOCUMENTS

4,467,031  8/1984  Gallati et al. ......................... 436/548

FOREIGN PATENT DOCUMENTS

2656155    6/1977   Fed. Rep. of Germany .
52-85163   7/1977   Japan .
52-85164   7/1977   Japan .
58-149700  9/1983   Japan .
8101469    5/1981   PCT Int'l Appl. ................. 436/548
2095831   10/1982   United Kingdom .

OTHER PUBLICATIONS

Engvall et al., (eds.), Scand. J. Immunol., Suppl. No. 7, vol. 8, (1978), pp. 7–20.
Ishikawa et al., J. Immunoassay, vol. 4, No. 3, (1983), pp. 209–265.
Krupey et al., Immunochemistry, vol. 9, (1972), pp. 617–622.
Carlsson et al., Biochem. J., vol. 173, (1978), pp. 723–737.
Carrico et al., Cancer Res., vol. 35, (1975), pp. 2928–2934.
Yoshitake et al., Analytical Letters, vol. 15, (1982), pp. 147–160.
Ishikawa et al.; Journal of Immunoassay 4, pp. 250–264 (1983).
Kitagawa et al., J. Biochem., 79, 233–236 (1976).
Yoshitake et al., Eur. J. Biochem., 101, 395–399 (1979).

*Primary Examiner*—Robert J. Warden
*Assistant Examiner*—Stephen C. Wieder
*Attorney, Agent, or Firm*—Wenderoth, Lind & Ponack

[57] ABSTRACT

An immunochemical assay of human carcinoembryonic antigen (CEA), comprising the use of an antibody supported on a carrier and an antibody labelled with peroxidase by coupling by means of a compound of the formula:

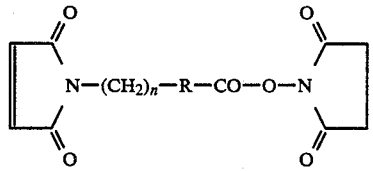

wherein n is an integer of 0 to 5 and R is a chemical bond or a divalent 6-membered cyclic hydrocarbon residue, in which at least one of said antibodies is a monoclonal antibody. The assay can be conducted with high sensitivity by simple and easy operation in clinical laboratories.

10 Claims, 1 Drawing Sheet

IMMUNOCHEMICAL ASSAY OF CARCINOEMBRYONIC ANTIGEN AND REAGENT THEREFOR

This invention relates to an immunochemical assay of human carcinoembryonic antigen (hereinafter sometimes referred to by the abbreviation CEA) by the sandwich method and to reagents thereof.

CEA was found in 1965 by Gold and colleagues in the perchloric acid extract of a human colonic cancer tissue. It occurs also in the digestive tract epithelium at the fetal stage. Therefore, it was named "carcinoembryonic antigen". CEA is a glycoprotein having a molecular weight of about 180,000 and a sugar content of about 50%. CEA is often detected at relatively high levels in cancer tissues or body fluids of various cancer patients (e.g. patients with stomach cancer, colon cancer, pancreas cancer or lung cancer) and is frequently used as an index in cancer diagnosis and prognostication.

Heretofore, the sandwich method has been in frequent use in enzyme immunoassay (hereinafter sometimes referred to by the abbreviation EIA) of CEA. The sandwich method is carried out generally in the following manner. A test fluid containing an unknown amount of CEA is reacted with an excess amount of the antibody supported on a carrier (first reaction), followed by reaction with a known excess amount of antibody labelled with an enzyme (second reaction). The activity of that portion of the enzyme which is trapped on the carrier or free from the carrier is measured. The first and second reactions may be conducted either simultaneously or one after another.

The antibodies for use in the first and second reactions are antisera obtained from the same kind of animal, antisera obtained from different kinds of animals, one of such antisera plus one monoclonal antibody obtained by hybridization, or two monoclonal antibodies, for instance.

Hitherthofore, CEA has been purified, generally by the method of Krupey et al. [Immunochemistry, 9 (1972), p.617], namely by subjecting the perchloric acid extract of a human colon cancer tissue to an appropriate combination of techniques of gel chromatography, affinity chromatography and/or electrophoresis. However, CEA obtained by such method has a drawback in that it has possibly been denatured because of its exposure to a strongly acidic solvent during processing. For this reason, a method of extracting and purifying CEA under mild conditions has been reported [Cancer Research, 35 (1975), p. 928]. However, this method is complicated and its utility has not yet been established. Furthermore, the question as to whether the metastatic liver cancer tissue of the colon cancer origin, which is generally used as the human cancer tissue for extraction, is completely identical in properties with the primary cancer tissue can hardly be said to have been clearly answered. In addition, CEA-related antigens having antigenic determinant positions common to CEA have been discovered in normal tissues and in the meconium of the newborn infant and named NCA [nonspecific cross-reacting antigen; Proceedings of the National Academy of Sciences of the U.S.A., 69 (1972),p.2492], NCA-2 [nonspecific cross-reacting antigen-2; Journal of Immunology, 111 (1973), p.1926], and so forth. When an anti-CEA antibody capable of cross-reacting with these CEA-related antigens is used, its cross-reactivity exerts influence on measured CEA values, so that accurate measured values cannot be obtained.

The labelling enzyme to be used in EIA is desired to be one which is stable, allows high sensitivity assay and will not be damaged during labelling. So far, peroxidase, β-D-galactosidase, alkaline phosphatase and glucose oxidase, among others, have been used. Among them, peroxidase is in most frequent use since it is a very stable enzyme having a molecular weight of about 40,000 and high enzyme activity.

In utilizing peroxidase in EIA, it is necessary to couple peroxidase with an immunochemically active substance in advance. However, each conventional method therefor has a drawback, and improvements therein have been desired.

Under these circumstances, the present inventors conducted further investigations, and found that the use of two anti-CEA antibodies in EIA by the sandwich method, at least one of which antibodies is a monoclonal antibody, and the use of peroxidase as the label in said sandwich EIA, and the coupling of said peroxidase with the relevant antibody by means of a compound of the formula:

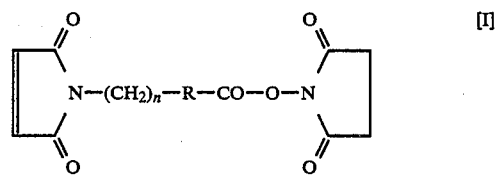

wherein n is an integer of 0 to 5 and R is a chemical bond or a divalent 6-membered-cyclic hydrocarbon residue, make it possible to assay CEA, even in trace amounts, with high sensitivity and accuracy. The inventors also found that when extracted from a CEA-containing cancer tissue with a nonionic surfactant-containing neutral salt solution, CEA can be purified without causing denaturation thereof, and that the use, in the above sandwich EIA, of a CEA-reacting monoclonal antibody produced by using the thus-purified CEA enables highly accurate CEA assay. Continued investigations based on these findings have now led to completion of the present invention.

The present invention relates to:

(1) In an immunochemical assay of human carcinoembryonic antigen which comprises adding a test sample to a first antibody reactive to human carcinoembryonic antigen supported on a carrier, adding a second antibody reactive to human carcinoembryonic antigen labeled with a labeling agent to the resultant mixture, and determining enzymatic activity of the resultant product, an improvement which comprises that said first antibody and said second antibody are dissimilar antibodies which are not overlapping with each other in antigen-determinant position (a particular region of an antigen at which the antigen reacts with an antibody at the reaction site of the antibody); that at least one of said two antibodies is a monoclonal antibody; that said labeling agent is a peroxidase; and that said peroxidase is coupled with said second antibody by means of a compound of the formula:

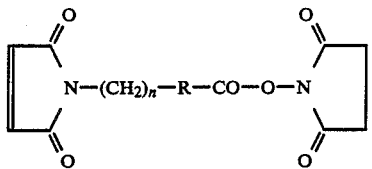

wherein n is an integer of 0 to 5 and R is a chemical bond or a divalent 6-membered cyclic hydrocarbon residue, (2) An immunochemical assay of human carcinoembryonic antigen as set forth in (1), wherein said monoclonal antibody is a human carcinoembryonic antigen-reactive monoclonal antibody obtained from hybridoma cells resulting from hybridization of myeloma cells with lymphocytes of a mammalian animal immunized with human carcinoembryonic antigen prepared by extracting the human carcinoembryonic antigen from a cancer tissue containing the antigen with a nonionic surfactant-containing neutral salt solution;

(3) A reagent set for immunochemical assay of human carcinoembryonic antigen, which comprises [1] the product of coupling of a peroxidase with an antibody by means of a compound [I]; and [2] an antibody supported on a carrier reactive with human carcinoembryonic antigen but differing in antigen determinant position from the antibody to be coupled with said peroxidase, at least one of said two antibodies being a monoclonal antibody;

(4) A method for purifying human carcinoembryonic antigen, which comprises purifying by extracting the human carcinoembryonic antigen from a cancer tissue containing the antigen with a nonionic surfactant-containing neutral salt solution;

(5) A human carcinoembryonic antigen-reactive monoclonal antibody, which is obtained from hybridoma cells resulting from hybridization of myeloma cells with lymphocytes of a mammalian animal immunized with human carcinoembryonic antigen prepared by extracting the human carcinoembryonic antigen from a cancer tissue containing the antigen with a nonionic surfactant-containing neutral salt solution;

(6) A method for producing human carcinoembryonic antigen-reactive monoclonal antibody, which comprises extracting the human carcinoembryonic antigen from a cancer tissue containing the antigen with a nonionic surfactant-containing neutral salt solution, immunizing a mammalian animal with the human carcinoembryonic antigen, producing hybridoma cells from lymphocytes thus obtained and myeloma cells, and cloning the hybridoma cells; and (7) Use of a human carcinoembryonic antigen-reactive monoclonal antibody obtained from hybridoma cells resulting from hybridization of myeloma cells with lymphocytes of a mammalian animal immunized with human carcinoembryonic antigen prepared by extracting the human carcinoembryonic antigen from a cancer tissue containing the antigen with a nonionic surfactant-containing neutral salt solution in the immunochemical assay of human carcinoembryonic antigen using an antibody suported on a carrier, the antigen and an antibody labelled with a labeling agent, which use comprises in that said human carcinoembryonic antigen-reactive monoclonal antibody is used as at least one of the antibodies to be supported on a carrier and the antibody to be labelled, which differ in antigen determinant position from each other without overlapping therein, that the label is a peroxidase, and that said label is coupled with the relevant antibody by means of a compound [I].

The monoclonal antibody to be used in accordance with the invention is more preferably a human carcinoembryonic antigen-reactive monoclonal antibody obtained from hybridoma cells resulting from hybridization of myeloma cells with lymphocytes of a mammalian animal immunized with a human carcinoembryonic antigen prepared by extracting the human carcinoembryonic antigen from a cancer tissue containing the antigen with a nonionic surfactant-containing neutral salt solution.

In peroxidase-antibody coupling in accordance with the invention, the peroxidase more preferably contains a thiol group introduced therein in advance.

The carrier for the antibody supported on a carrier to be used in accordance with the invention includes, among others, gel particles, such as agarose gel [e.g. Sepharose 4B, Sepharose 6B (Pharmacia Fine Chemicals, Sweden)], dextran gel [e.g. Sephadex G-75, Sephadex G-100, Sephadex G-200 (Pharmacia Fine Chemicals, Sweden)] and polyacrylamide gel [e.g. Biogel P-30, Biogel P-60, Biogel P-100 (Bio-Rad Laboratories, U.S.A.)]; cellulose particles [e.g. Avicel (Asahi Chemical Industry), ion exchange cellulose (e.g. diethylaminoethylcellulose, carboxymethylcellulose)]; physical adsorbents, such as glass (e.g. glass bead, glass rod, aminoalkylated glass bead, aminoalkylated glass rod), silicone piece, styrenic resin (e.g. polystyrene bead, polystyrene particle) and immunoassaying plate (e.g. product of Nunc, Denmark); and ion exchange resins, such as weakly acidic cation exchange resin [e.g. Amberlite IRC-50 (Rohm and Haas, U.S.A.), Zeokarb 226 (Permutit, West Germany)] and weakly basic anion exchange resin [e.g. Amberlite IR-4B, Dowex 3 (Dow Chemical, U.S.A.)].

The antibody supported on a carrier can be prepared by using any known conventional method, such as the cyanogen bromide method or glutaraldehyde method as described, for example, in "Taisha" (Metabolism and Disease), 8 (1971), 696. Nalayama Shoten Inc. Japan. An easier method may consist in physical adsorption on the carrier surface.

In accordance with the invention, either a monoclonal anti-CEA antibody or a polyclonal anti-CEA antibody may be used. As the antigen for the immunization for antibody production, there is used CEA purified by a per se known method [Krupey et al., Immunochemistry, 9 (1972), 617]. However, preferably use is made of a CEA fraction purified by extracting it from a human cancer tissue with a nonionic surfactant-containing neutral salt solution.

As the human cancer tissue, any CEA-containing human cancer tissue may be used but particularly desirable is a human colon cancer tissue. The colon cancer tissue may be at any stage, but preferably at the stage of Dukes C or D.

As the nonionic surfactant, there may be used any one which is capable of solubilizing cell constituents. Particularly preferred are nonionic surfactants having ethylene oxide units [—$(CH_2—CH_2—O)_n$— wherein n is an integer] [e.g. Tween 20, Tween 40, Tween 80, Triton N-101, Triton X-100, Lobrol WX, Briji 96, etc., available from Sigma (U.S.A.)].

As the neutral salt, there may favorably be used sodium chloride, potassium chloride or sodium sulfate, for instance. The extraction solvent is preferably about 0.05M to 3M sodium chloride or potassium chloride containing about 0.1 to 4% nonionic surfactant having ethylene oxide units, which is used in an amount of about 1 to 10 volumes based on the volume of human cancer tissue.

The efficiency of CEA extraction may be increased by stirring, shaking, sonication, or some other adequate treatment.

The CEA extract obtained in the above manner can be further purified by any known purification process (e.g. gel chromatography, affinity chromatography, gel electrophoresis) [cf. Immunochemistry, 9 (1972), p.617; Cancer Research, 35 (1975), p.2928].

Such purification process can increase the purity of CEA to several percent to several tens percent on the protein basis.

The monoclonal anti-CEA antibody can be produced essentially by the method of Milstein et al. [Nature, 256 (1975), p.495. For example, hybridomas secreting monoclonal anti-CEA antibodies can be produced by immunizing a mouse using the above purified CEA as the antigen and hybridizing spleen cells from the immunized mouse with mouse myeloma cells.

Thus, spleen cells of a mouse (e.g. BALB/C strain) previously immunized with purified CEA are mixed with myeloma cells (e.g. NS-1, PS-Ul) in the presence of a hybridization inducer (e.g. polyethylene glycol, Sendai virus), and the mixture is incubated for effecting hybridization, whereby hybridomas are obtained. The mixing ratio between spleen cells and myeloma cells is advantageously about 1:1 to about 10:1.

Examples of the hybridoma obtained in accordance with the present invention include Mo 272-11 (monoclonal antibody Mo-T2), and Mo 221-73 (monoclonal antibody Mo-T3), which are obtained in Example 1-(2) hereinafter mentioned. Said hybridoma Mo 272-11 (monoclonal antibody Mo-T2) has been deposited at the Institute for Fermentation, Osaka(IFO), Japan as of Mar.4, 1985 under the accession number of IFO 50033.

Selective hybridoma growth can be effected by using hypoxanthine-aminopterin-thymidine medium [HAT medium; Nature, 256 (1975), p.495], for instance.

The cell culture fluid can be checked for the presence of the desired antibody by the per se known enzyme immunoassay method. The hybridomas capable of producing antibodies highly specific to CEA are further made monoclonal by the conventional limiting dilution technique. The desired hybridoma obtained can grow in conventional liquid media or in the peritoneal cavity of mammals. The monoclonal antibody produced by the hybridoma is concentrated and purified by known methods ( e.g. salting out with ammonium sulfate, DEAE-cellulose column chromatography).

As the monoclonal antibody, there is chosen an antibody highly reactive with CEA but by far less reactive with test samples from normal tissues or non-cancer-bearing patients. When two monoclonal antibodies are used in EIA by the sandwich technique, they are chosen such that they differ in antigen determinant position.

The polyclonal anti-CEA antibody can be prepared by the conventional method. Thus, purified CEA is inoculated into a warm-blooded animal other than human. The warm-blooded animal other than human includes warm-blooded mammals (e.g. rabbit, sheep, rat, mouse, guinea pig, cattle, horse, pig), birds (e.g. chicken, pigeon, duck, goose, quail), etc. Said antigen is inoculated into such warm-blooded animals other than human in an amount effective to induce antibody production. Thus, for example, about 0.1 to 10 mg, per inoculation, of the antigen is emulsified in an equal-volume (1 ml) mixture of physiological saline and Freund's complete adjuvant and the emulsion is injected subcutaneously into the back and hind leg palms of a rabbit, for instance, 5 times at 4-week intervals, whereby antibody production can be induced in many cases.

For recovering the antibody thus produced in a warm-blooded animal, blood is collected from the auricular vein (in the case of rabbit), for instance, generally 7 to 12 days after final inoculation and centrifuged to give a serum. The antiserum obtained is salted out by a known method, generally followed by affinity chromatography using a CEA supported on a carrier. Recovery of the adsorbed fraction can give purified polyclonal anti-CEA antibody.

One of the two antibodies to be used in accordance with the invention is monoclonal anti-CEA antibody. The other antibody is polyclonal antibody or monoclonal antibody. The antibody molecule may also occur as immunoglobulin G (IgG), F(ab')$_2$, Fab' or Fab.

The thus-obtained anti-CEA monoclonal antibody can be used as a reagent in EIA of CEA by the sandwich method.

The peroxidase which serves as the label may be of any appropriate origin. Examples are peroxidases obtained from horseraddish, pineapple, fig, sweet potato, horsebean, corn, etc. Preferred among them is horseraddish peroxidase (HRP) extracted from the horseraddish.

In coupling the peroxidase with the antibody using the compound [I], it is favorable to use the peroxidase after introduction of a thiol group thereinto.

The thiol group introduction into peroxidase can be effected through the amino group of peroxidase. For instance, S-acetylmercaptosuccinic anhydride (hereinafter sometimes referred to by the abbreviation AMSA), N-succinimidyl 3-(2-pyridyldithio)propionate (hereinafter sometimes referred to by the abbreviation SPDP), or the like ordinary thiol group-introducing reagent is used with advantage.

Therefore, a certain group may intervene between the thiol group and peroxidase, depending on the particular thiol group-introducing reagent employed.

When AMSA is used, about 0.1 to 10 mg of peroxidase is dissolved in about 0.2 to 2 ml of neutral buffer (e.g. 0.1M phosphate buffer), a solution of about 0.1 to 4 mg of AMSA in about 0.01 to 0.1 ml of N,N-dimethylformamide is added, and the reaction is effected at about 4° to 35° C. for about 10 to 120 minutes. Then, following addition of about 0.2 to 2M hydroxylamine, the reaction is allowed to progress at about 4° to 35° C. for about 1 to 60 minutes. Purification by gel chromatography gives thiolated peroxidase.

When SPDP is used, about 0.1 to 10 mg of peroxidase is dissolved in about 0.1 to 1 ml of neutral buffer (e.g. 0.1M phosphate buffer), and an ethanolic solution containing about 0.1 to 3 mg of SPDP is added, followed by about 10 to 240 minutes of reaction at about 4° to 35° C. After removal of the excess reagent by gel chromatography, reduction is effected by adding a reducing agent such as dithiothreitol. Further purification of the reduction product by gel chromatography gives thiolated peroxidase.

Referring to the compound of the formula:

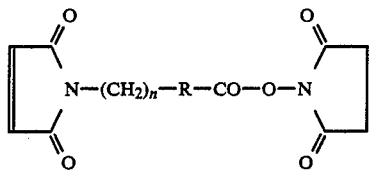

wherein n and R are as defined above, which is used in coupling peroxidase with the antibody, the divalent 6-membered cyclic hydrocarbon residue represented by R in the above formula may be saturated or unsaturated. Examples of the saturated divalent 6-membered cyclic hydrocarbon residue are 1,2-,.1,3- and 1,4-cyclohexylene, and examples of the unsaturated divalent 6-membered cyclic hydrocarbon residue are 1,2-, 1,3- and 1,4-phenylene.

In said compound [I], n is preferably an integer of 1 to 5, more preferably 1. R is preferably a divalent 6-membered cyclic hydrocarbon residue, in particular 1,4-cyclohexylene.

The compound [I] to be used in carrying out the method of the invention can be produced, for example, by the method described in The Journal of Biochemistry, 79 (1976), p. 233, European Journal of Biochemistry, 101 (1979), p. 395, Japanese patent application Laid-open No. Sho 52(1977)-85,163, Japanese patent application Laid-open No. Sho 52(1977)-85,164, German patent application Offenlegungsschrift No. 2656155 or a modification thereof. For instance, said compound can be produced by reacting a maleimide compound [II] of the formula:

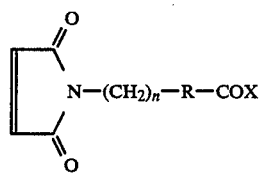

wherein X is a hydroxyl group or a halogen atom and n and R are as defined above, with a succinimide compound [III] of the formula:

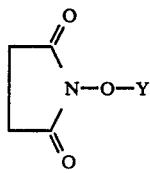

wherein Y is a hydrogen atom or an alkali metal atom, in the presence of a dehydrating agent or a deacidifying agent. Referring to the above general formulas, the halogen atom is, for example, a chlorine or bromine atom, and the alkali metal atom is, for example, a sodium or potassium atom. The dehydrating agent to be used for the above reaction includes, among others, sulfuric acid and dicyclohexylcarbodiimide, and the deacidifying agent includes pyridine and triethylamine, amongst others.

The above compound [II] can be produced, for example, by the method described in Japanese patent application Laid-open No. Sho 52(1977)-85,164 or a modification thereof. Thus, for instance, said compound can be obtained by subjecting a compound [IV] of the formula:

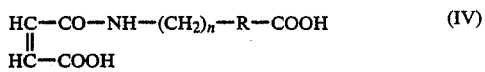

wherein n and R are as defined above, to dehydration with ring closure. The dehydration with ring closure can be effected by gentle heating in the presence of a dehydrating agent such as acetic anhydride or acetic anhydride plus sodium acetate (anhydrous).

Alternatively, the compound [II] can be produced by the method described in Helvetica Chimica Acta, 58 (1975), p. 531 or a modification thereof. Thus, for example, an N-alkoxycarbonylmaleimide [V] of the formula:

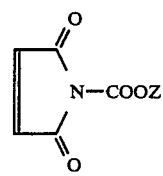

wherein Z is an alkyl group, is reacted with an amino acid [VI] of the formula:

wherein n and R are as defined above, to give a maleimide compound [VII] of the formula:

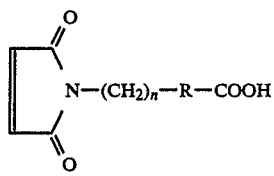

wherein n and R are as defined above. Thereto is added the succinimide compound of the formula [III], and the reaction is carried out in the presence of a dehydrating agent or deacidifying agent such as mentioned hereinabove, whereby the compound [II] can be produced.

Referring to the above general formula [V], the alkyl group represented by Z is, for example, methyl or ethyl.

In reacting the thiolated peroxidase with anti-CEA antibody, anti-CEA antibody IgG or F(ab')$_2$ fraction (obtained by treatment with pepsin) is reacted with compound [I] in a buffer having a pH of about 6 to 8 at about 10° to 50° C. for about 10 minutes to 24 hours. Said buffer is, for example, 0.1M phosphate buffer of pH 6.5 or 0.05 M phosphate buffer of pH 6.3.

The thus-obtained maleimidated anti-CEA antibody can be purified by gel chromatography, for instance. As the packing for use in said gel chromatography, there may be mentioned Sephadex G-25 [Pharmacia Fine Chemicals (Sweden)] and Biogel P-2 [Bio-Rad Laboratories (U.S.A.)], among others.

In the next place, the reaction of the maleimidated anti-CEA antibody with the thiolated peroxidase can be conducted in a buffer at a temperature of about 0° to 40° C. for about 1 to 48 hours. As the buffer, there may be mentioned, for example, 0.1M phosphate buffer containing 5mM sodium ethylenediaminetetraacetate and having a pH of 6.0.

The reaction of peroxidase with compound [I] is carried out in a buffer having a pH of about 6 to 8 at about 10° to 50° C. for about 10 minutes to 24 hours. Said buffer is, for example, 0.1M phosphate buffer of pH 7.0 or 0.05M phosphate buffer of pH 6.3.

The thus-obtained maleimidated peroxidase can be purified by gel chromatography, for instance. As the packing for use in said gel chromatography, there may be mentioned Sephadex G-25 [Pharmacia Fine Chemicals (Sweden)] and Biogel P-2 [Bio-Rad Laboratories (U.S.A.)], among others.

In reacting the maleimidated peroxidase with anti-CEA antibody, anti-CEA antibody IgG or F(ab')$_2$ fraction (obtained by treatment with pepsin) is reduced in the presence of a mercaptoethylamine and the anti-CEA antibody IgG or Fab' purified by gel chromatography is reacted with the maleimidated peroxidase.

Said reaction can be conducted in a buffer at a temperature of about 0° C. to 40° C. for about 1 to 48 hours. As the buffer, there may be mentioned, for example, 0.1M phosphate buffer containing 5 mM sodium ethylenediaminetetraacetate and having a pH of 6.0.

The thus-produced peroxidase-labelled antibody can be purified, for example, by gel chromatography. The carrier to be used in said gel chromatography includes, but is not limited to, Ultrogel AcA44 [LKB (France)] and Sephacryl S-200 [Pharmacia Fine Chemicals (Sweden)].

The assay method according to the invention is illustrated in further detail in the following.

Firstly, [1]: A CEA-containing object of assay is added to the antibody supported on a carrier to thereby effect the antigen-antibody reaction, followed by addition of the peroxidase-coupled anti-CEA antibody obtained in the above for further reaction.

The CEA-containing test sample, which is the object of assay by the enzyme immunoassay method according to the invention, includes, but is not limited to, urine, serum, plasma, spinal fluid and various organ extracts. In particular, urine, serum and plasma are used most often.

[2]: A substrate for peroxidase is added to the reaction product obtained in step [1], and the absorbance or fluorescence intensity of the resultant substance is measured, whereby the enzyme activity of the above reaction product can be known.

[3]: A standard curve indicative of the relation between CEA level and absorbance or fluorescence intensity is constructed in advance by using standard solutions containing known quantities of CEA and following the above procedure [1] and [2].

[4]: The absorbance or fluorescence intensity obtained for the assay object containing an unknown quantity of CEA is compared with the standard curve to thereby determine the CEA content in the object of assay.

The assay kit for use in the immunochemical assay of CEA by the sandwich method according to the invention includes for example,

[A]: An assay kit which principally comprises:
(1) An anti-CEA antibody supported on a carrier;
(2) The peroxidase-labelled anti-CEA antibody obtained by the method of the invention (coupled by means of the compound [I]);
(At least one of the above two antibodies (1) and (2) is a monoclonal antibody.)
(3) Standard CEA;
(4) Buffers for diluting the reagents mentioned above under (2) and (3) and the test sample. The buffers, are for example phosphate or glycine buffer having a pH of about 6 to 9 and containing serum plus proteinic substances, for example about 10% bovine serum plus about 1% bovine serum albumin (hereinafter sometimes referred to by the abbreviation BSA)]; and
(5) Reagents necessary for peroxidase activity measurement: for instance, p-hydroxyphenylacetic acid (enzyme substrate) and hydrogen peroxide for the fluorescence method, o-phenylenediamine and hydrogen peroxide for the colorimetric method; a buffer for dissolving the enzyme substrate (preferably phosphate buffer or citrate buffer): and an enzymatic reaction terminator solution;

[B]: An assay kit which principally comprises
(1) An anti-CEA antibody supported on a carrier;
(2) The peroxidase-labelled anti-CEA antibody obtained by the method of the invention (product of coupling of thiolated peroxidase with anti-CEA antibody by means of the compound [I]);
(3) Standard CEA;
(4) Buffers for diluting the reagents mentioned above under (2) and (3) and the test sample. The buffers are for example phoshate or glycine buffer having a pH of about 6 to 9 and containing serum plus proteinic substances, for example about 10% sheep serum plus about 1% bovine serum albumin); and
(5) Reagents necessary for peroxidase activity measurement: for instance, p-hydroxyphenylacetic acid (enzyme substrate) and hydrogen peroxide for the fluorescence method, o-phenylenediamine and hydrogen peroxide for the colorimetric method; a buffer for dissolving the enzyme substrate (preferably phosphate buffer or citrate buffer); and an enzymatic reaction terminator solution; or, further,

[C]: An assay kit which principally comprises
(1) An anti-CEA antibody supported on a carrier;
(2) The peroxidase-labelled anti-CEA antibody obtained by the method of the invention (product of coupling of thiolated peroxidase with anti-CEA antibody by means of the compound [I]);
(At least one of the above two antibodies (1) and (2) is a monoclonal antibody.)
(3) Standard CEA;
(4) Buffers for diluting the reagents mentioned above under (2) and (3) and the test sample. The buffers are for example phosphate or glycine buffer having a pH of about 6 to 9 and containing serum plus proteinic substances, for example about 10% sheep serum plus about 1% bovine serum albumin); and
(5) Reagents necessary for peroxidase activity measurement: for instance, p-hydroxyphenylacetic acid (enzyme substrate) and hydrogen peroxide for the fluorescence method, o-phenylenediamine and hydrogen peroxide for the colorimetric method; a buffer for dissolving the enzyme substrate (preferably phosphate buffer); and an enzymatic reaction terminator.

The above kit can be used, for example, in the following manner:

Dilute the standard CEA or test sample by adding about 10 to 200 μl of the reagent (4), add a prescribed amount of the reagent (1), and allow the reaction to proceed at about 0° to 40° C. for about 1 to 48 hours. Wash the carrier with water, add about 10 to 300 μl of the reagent (2), and allow the reaction to progress at about 0° to 40° C. After about 1 to 48 hours of reaction, wash the carrier, and assay the activity of carrier-bound peroxidase; namely add about 10 to 1000 μl of a peroxidase substrate solution, allow the reaction to proceed at about 20° to 40° C. for about 0.2 to 24 hours, then terminate the enzymatic reaction, and measure the reaction mixture for absorbance or fluorescence intensity.

The use of the reagents for immunochemical assay enables high-sensitivity assay of CEA by simple and easy operation in ordinary clinical laboratories.

The use of the reagents according to the invention enables highly sensitive and accurate assay of CEA and the reagents are very useful in the diagnosis and prognostication of digestive organ cancer, such as colon cancer, and cancer of other organs by simple and easy operation in clinical laboratories. Thus, when used in the assay of CEA, the peroxidase-labelled antibody according to the invention brings about only small blank values owing to their limited nonspecific adsorption on the solid phase, whereby the reliability of the assay is increased. The monoclonal antibody obtained in accordance with the invention has strong affinity for CEA but by far limited cross reactivity to other CEA-related antigens and therefore is hardly influenced by CEA-related antigens concurrently present in test samples. Furthermore, since such monoclonal antibody is used as one of the reagent constituents, product supply is easy and the reproducibility of assay is high.

The present method for purifying CEA brings high yield of the objective CEA.

Moreover, the monoclonal anti-CEA antibody produced by using, CEA as the immunogen obtained by the method of the invention, is highly reactive with CEA, and the frequency of its being a monoclonal anti-CEA antibody having no cross-reactivity with the CEA-related antigens NCA and NCA-2 is high. Therefore, the method of the invention is useful in monoclonal anti-CEA antibody production.

Such selected monoclonal anti-CEA antibody can be used as a constituent of an immunochemical diagnostic reagent kit. In enzyme immunoassay by the sandwich technique, for instance, the monoclonal anti-CEA antibody can be used as the antibody supported on a carrier and/or the enzyme-labelled antibody. Such diagnostic reagent can be used, for example, in the diagnosis and prognostication of digestive organ cancer, such as colon cancer, or some other cancer. Furthermore, said antibody can also be used for therapeutic purposes.

REFERENCE EXAMPLE 1

Figure 1:
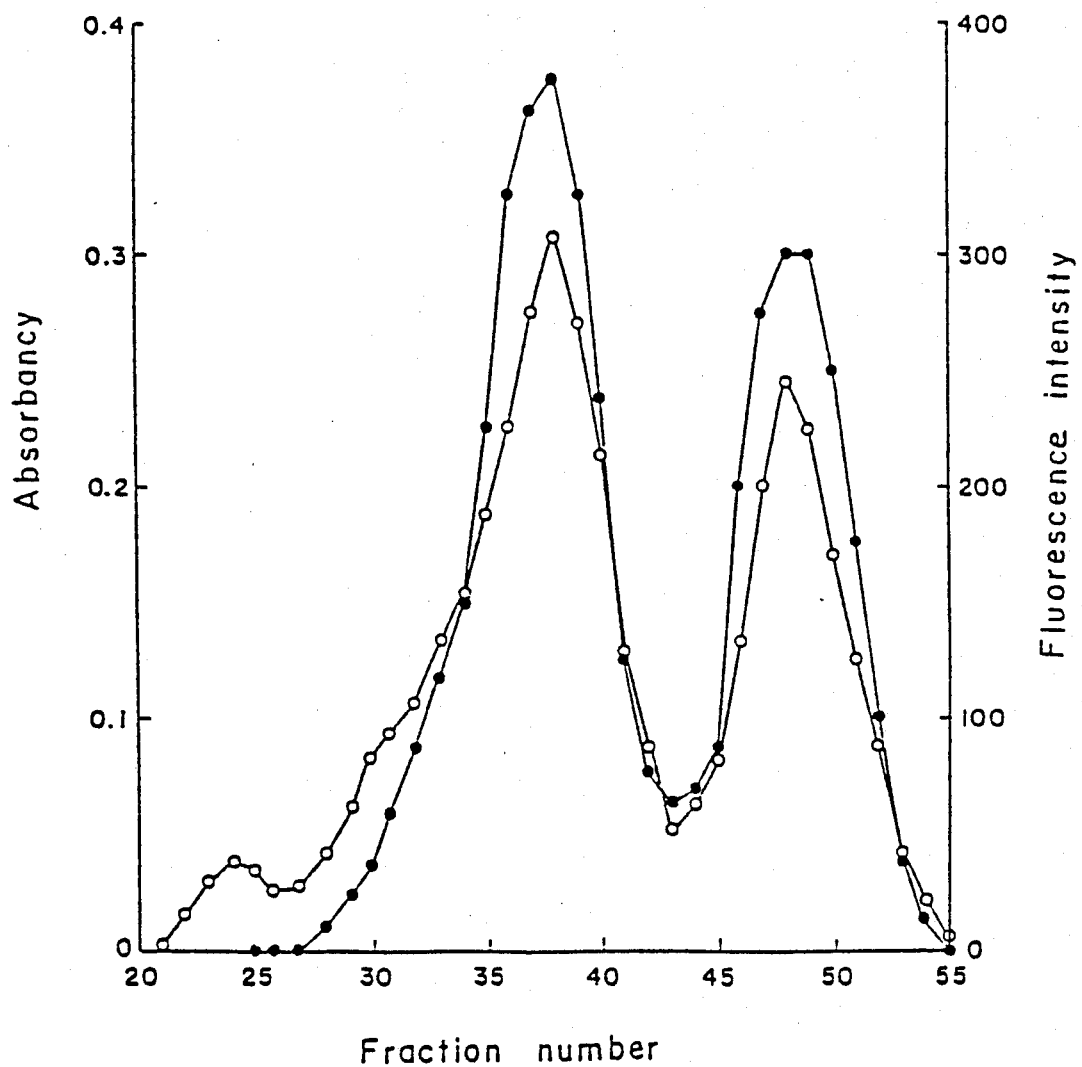
FIG. 1 shows the elution pattern in gel chromatography of the reaction product between peroxidase and polyclonal anti-CEA antibody (Fab' fragment) as obtained in Example 1-(5).

Purification by perchloric acid extraction and production of monoclonal antibody (1) Purification of antigen CEA was purified by the method of Krupey et al. [Immunochemistry, 9 (1972), 617]. Thus, to 100 g of colon cancer tissue cut to pieces, 400 ml of distilled water was added, and the mixture homogenized using a homogenizer with ice cooling for 1 hour. To the thus-prepared suspension was added the same volume of 2M perchloric acid and extraction was effected at room temperature for 30 minutes. The suspension was centrifuged, and the supernatant dialyzed against distilled water and then lyophilized. The lyophilizate was subjected to gel chromatography on a Sepharose 4B [Pharmacia (Sweden)] column (2.3 cm × 100 cm) using 0.05M phosphate buffer containing 0.15M NaCl. CEA-containing fractions were combined, dialyzed, lyophilized, and further subjected to gel chromatography on a Sephadex G-200 column (2.3 cm × 100 cm). CEA eluate fractions were combined, dialyzed and lyophilized to give purified CEA antigen (3 mg).

(2) Production of monoclonal anti-CEA antibody

A 70 μg portion of the purified antigen obtained above in (1) was dissolved in 150 μl of physiological saline. Thereto was added 250 μl of Freund's complete adjuvant [Tachibana et al.: "Men-eki no Seikagaku (Biochemistry of Immunity)", page 26, (1967) Kyoritsu Shuppan Inc., Japan]. After thorough mixing, the emulsion obtained was subcutaneously administered to a BALB/C mouse. The mouse was further immunized two times with Freund's incomplete adjuvant at 2-week intervals. The final immunization was carried out by intravenous administration of a solution of 130 μg of the purified antigen in 400 μl of physiological saline. Three days later, the spleen was excised and the spleen cells were washed well with Dulbecco's modified MEM medium. Said spleen cells ($1 \times 10^8$ cells) were mixed with $2 \times 10^7$ myeloma cells (P3U1). The subsequent centrifugation at 700 rpm for 15 minutes gave a pellet. Thereto was added 0.4 ml of a 45% solution of polyethylene glycol 6000 in RPMI-1640, followed by gradual addition of a further 15 ml portion of RPMI-1640 for dilution. The mixture was centrifuged at 700 rpm for 15 minutes, and the cells obtained were suspended in 100 ml of RPMI-1640 medium containing 20% fetal bovine serum. The cell suspension was distributed, in 2.0 ml portions, into the wells of 24-well incubation plates [Flow (U.S.A.)]. On the 2nd, 5th and 8th days, half volume of the culture supernatant was replaced with HAT medium. After 14 days of incubation, the supernatant was assayed for antibody titer. Of the total 120 wells, 12 wells were found to be positive.

These positive hybridoma clones were diluted with RPMI-1640 medium containing 20% fetal bovine serum and BALB/C mouse thymocytes as feeder cells added thereto. Repeated limiting dilution in this manner finally gave 12 kinds of hybridoma clones capable of producing monoclonal anti-CEA antibody. These were injected into the mineral oil-treated BALB/C mouse peritoneal cavity. Ascitic fluid collection after 2–3 weeks gave monoclonal anti-CEA antibodies. These monoclonal antibodies were salted out by the ammonium sulfate method to give the respective globulin fractions (Mo-K1 to Mo-K12).

REFERENCE EXAMPLE 2

Crosslinking using periodate

The method of Nakane et al. [The Journal of Histochemistry and Cytochemistry, 22 (1974), 1084] was followed. Thus, 7 mg of horseraddish peroxidase was dissolved in 1 ml of 0.3M sodium bicarbonate (pH 8.1), followed by addition of 0.1 ml of 1% 1-fluoro-2,4-dinitrobenzene. The reaction was allowed to proceed at room temperature for 1 hour. Then, 1 ml of 0.06M NaIO$_4$ was added, and the mixture was stirred at room temperature for 30 minutes. After addition of 1 ml of 0.16M aqueous ethylene glycol, the mixture was allowed to stand at room temperature for 1 hour and dialyzed against 0.01M sodium carbonate buffer (pH 9.5) overnight.

A solution of 5 mg of the monoclonal anti-CEA antibody gamma-globulin fraction (Mo-T3) obtained in Example 1-(2) to be mentioned later herein in 1 ml of 0.01M sodium carbonate buffer (pH 9.5) was mixed with the previously-prepared aldehyde peroxidase. After the reaction at room temperature for 3 hours, the mixture was added to 5 mg of sodium borohydride, followed by overnight reaction at 4° C. The reaction mixture was dialyzed against 0.01M phosphate buffer (pH 7.1) containing 0.15M NaCl at 4° C. overnight and then subjected to gel chromatography using an Ultrogel AcA44-packed column (1.5 cm×45 cm) with 0.1M phosphate buffer (pH 6.5) as the eluent. The eluate fractions were measured for absorbances at 280 and 403 nm and enzyme activity in the same manner as in Example 1-(5) to be described later, and the desired fractions were collected. The thus-obtained monoclonal anti-CEA antibody-HRP complex solution was adjusted to 0.1% BSA and 0.005% merthiolate, and stored at 4° C.

EXAMPLE 1

(1) Purification of antigen

To 200 g of colon cancer tissue cut to pieces, there was added 600 ml of 0.15M NaCl containing 1% Tween 20 [Sigma (U.S.A.)], followed by homogenization using a homogenizer with ice cooling for 10 minutes. The resultant suspension was further sonicated with ice cooling for 1 hour and then centrifuged at 12,000 rpm for 20 minutes. The supernatant was dialyzed against distilled water, lyophilized, and dissolved in 0.2M citrate buffer (pH 6.5). The solution was applied to a concanavalin A-bound Sepharose 4B [Pharmacia (Sweden)] column (2.2 cm×26 cm) as prepared using the same buffer. The substance retained on the column was eluted with α-methyl-D-mannoside-containing buffer. The eluate was dialyzed against distilled water and then lyophilized. The lyophilizate was subjected to gel chromatography using an Ultrogel AcA-34 [LKB (France)] column (2.3 cm x 100 cm) and 0.2M citrate buffer (pH 6.5), and the fractions 280–350 ml were combined, dialyzed against distilled water, and lyophilized to give purified CEA antigen (5 mg).

(2) Production of monoclonal anti-CEA antibody

To a solution of 70 μg of the purified antigen obtained in the foregoing paragraph (1) in 150 μl of physiological saline, there was added 250 μl of Freund's complete adjuvant [Tachibana et al.: "Men-eki-no-Seikagaku (Biochemistry of Immunity)", page 26, (1967) Kyoritsu Shuppan Inc.)], followed by thorough mixing. The resultant emulsion was subcutaneously administered to a BALB/C mouse, followed by further two immunizations with Freund's incomplete adjuvant at 2-week intervals. The final immunization was carried out by intravenous administration of a solution of 130 μg of purified antigen in 400 μl of physiological saline. Three days later, the spleen was excised. The spleen cells were washed well with Dulbecco's modified MEM medium and 1×10⁸ cells thereof were mixed with 2×10⁷ mouse myeloma cells (P3U1). The mixture was centrifuged at 700 rpm for 15 minutes to give a pellet. To this was added 0.4 ml of a 45% solution of polyethylene glycol 6000 in RPMI-1640, followed by further gradual addition of 15 ml of RPMI-1640 for dilution. Cells were collected by centrifugation at 700 rpm for 15 minutes and suspended in 100 ml of RPMI-1640 medium containing 20% fetal bovine serum. The cell suspension was distributed, in 2.0 ml portions, into the wells of 24-well incubation plates [Flow (U.S.A.)]. On days 2, 5 and 8 of incubation, half, in volume, of each culture supernatant was replaced with HAT medium. After 14 days of incubation, the culture supernatant was assayed for antibody titer and 9 wells out of the total 72 wells were found to be positive.

These positive hybridoma clones were each diluted with RPMI-1640 medium containing 20% fetal bovine serum and BALB/C mouse thymocytes as feeder cells. Repeated limiting dilution finally gave 5 kinds of hybridoma clones capable of producing monoclonal anti-CEA antibody. These were injected into the mineral oil-treated BALB/C mouse peritoneal cavity. Ascitic fluid collection 2-3 weeks later gave monoclonal anti-CEA antibodies. These monoclonal antibodies were salted out by the ammonium sulfate method to give the respective globulin fractions (Mo-T1 to Mo-T6).

(3) Production of polyclonal anti-CEA antibody

To a solution of 200μg of the purified antigen obtained in the foregoing paragraph (1) in 1 ml of physiological saline, there was added 1 ml of Freund's complete adjuvant, followed by thorough mixing. The resultant emulsion was administered to a rabbit by intramuscular injection into both femurs and subcutaneous injectioh at several sites on the back. The above procedure was repeated five times at 3-week intervals and, 1 week after the final immunization, blood was collected to give an antiserum. A globulin fraction was prepared by salting out by the ammonium sulfate method and subjected to affinity chromatography using a CEA-bound Sepharose 4B column. Elution of the antibody fraction retained on the column with 0.17M glycine-hydrochloride buffer (pH 2.3) gave a polyclonal antibody having strong affinity for CEA.

(4) Comparison in reactivity of monoclonal antibodies

The monoclonal antibodies obtained in the preceding paragraph (2) and Reference Example 1 were examined for reactivity with CEA and related antigens.

Reagents:

(1) Microplates sensitized with the monoclonal anti-CEA antibodies obtained in the preceding paragraph (2) and Reference Example 1;

(2) Horseradish peroxidsase (hereinafter referred to by the abbreviation HRP)-labelled anti-CEA antibody complex [DAKO Biochemicals (Denmark)];

(3) CEA and CEA-related antigens;

(4) Buffer B (0.02M phosphate buffer, pH 7.0, containing 10% bovine serum and 0.15M NaCl) and buffer A (0.02 M phosphate buffer containing 0.15M NaCl);

(5) Reagents necessary for peroxidase activity measurement: 0.1M Citric acid-disodium phosphate buffer, pH 4.8, containing 0.02% hydrogen peroxide and 0.15% o-phenylenediamine, and reaction terminator solution (2 N sulfuric acid).

Preparation of antibody-sensitized microplates:

A solution of the monoclonal anti-CEA antibody of the preceding paragraph (2) or Reference Example 1 as prepared by dilution with 0.1M carbonate buffer (pH 9.6) to 50 μg/ml was distributed, in 100 μl portions, into the wells of an immunoplate I for EIA [Nunc (Denmark)], and the plate was allowed to stand at 4° C. overnight for sensitization. After washing the wells with 0.01M phosphate buffer (pH 7.0) containing 0.1% BSA, the plate was stored in the cool place until use thereof. Measurement:

A standard solution of CEA in buffer B was distributed, in 100 μl portions, into the wells. After 3 hours of reaction at 37° C., the wells were washed with buffer A, followed by addition of an HRP-labelled anti-CEA complex solution in 100 μl portions (30 ng as HRP per well). After 3.5 hours of further reaction at 25° C., the wells were washed with buffer A. To each well was added 100 μl of 0.1M citric acid-disodium phosphate buffer (pH 4.8) containing 0.02% hydrogen peroxide and 0.15% o-phenylenediamine. After 30 minutes of incubation at 30° C., the reaction was terminated by adding 100 μl per well of 2 N sulfuric acid, followed by absorbance measurement at 490 nm, with a blank as the control, using an automatic colorimeter for microplates [Titertek Multiskan; Flow (U.S.A.)].

The results obtained, which are shown in Table 1, indicate that 4 out of the 6 monoclonal anti-CEA antibodies obtained above in (2) did not react with the CEA-related antigen NCA (nonspecific cross-reacting antigen) or NCA-2 (nonspecific cross-reacting antigen-2) and that the invention can provide CEA-specific monoclonal anti-CEA antibodies with high probability. On the other hand, 11 out of the 12 monoclonal anti-CEA antibodies obtained in Reference Example 1 reacted with the CEA-related antigens. Only one antibody (Mo-K6) did not react either with NCA or with NCA-2.

TABLE 1

| Monoclonal antibody | NCA | Meconium NCA | NCA-2 |
|---|---|---|---|
| Mo-K1 | − | + | + |
| K2 | − | + | + |
| K3 | + | + | + |
| K4 | − | − | + |
| K5 | − | + | + |
| K6 | − | − | − |
| K7 | + | + | + |
| K8 | + | + | + |
| K9 | + | + | + |
| K10 | − | − | + |
| K11 | − | + | + |
| K12 | − | + | + |
| Mo-T1 | + | + | + |
| T2 | − | − | − |
| T3 | − | − | − |
| T4 | − | − | − |
| T5 | + | + | + |
| T6 | − | − | − |

+: Reacting,
−: Not reacting (5) Production of polyclonal anti-CEA antibody (Fab′)-HRP complex (a) Introduction of maleimido group Horseraddish peroxidase [6 mg; Boehringer Mannheim (West Germany)] was dissolved in 1 ml of 0.1M phosphate buffer (pH 7.0), followed by addition of a solution of 4.8 mg of the coupling agent MMC (the compound of the general formula [I], n=1, R=cyclohexylene) in 50 μl of N,N-dimethylformamide. The mixture was stirred at 30° C. for 60 minutes. The resultant precipitate was removed by centrifugation and the supernatant was applied to a Sephadex G-25 column (1.0×45 cm), followed by elution with 0.1M phosphate buffer. Protein-containing fractions were combined and concentrated using a collodion membrane. The thus-prepared maleimidated peroxidase contained 1.0 to 1.2 maleimido groups introduced therein per molecule of peroxidase (calculated on the assumption that the molecular weight of peroxidase=40,000 and $E_{1\%}^{280nm}=22.75$).

(b) Production of maleimidated peroxidase-anti-CEA anti-body (Fab′ fragment) complex To 5 mg of the polyclonal anti-CEA antibody obtained above in (3), there was added 0.1 mg of pepsin. After overnight reaction at 30° C., the product was purified on a Sephadex G-150 column (2.5 cm in diameter, 55 cm in length). The antibody F(ab′)₂ fraction obtained was reduced with 2-mercaptoethylamine, followed by purification by gel chromatography using a Sephadex G-25 column. Thus was obtained rabbit anti-CEA antibody (Fab′ fragment).

A 1.5 mg portion of the maleimidated peroxidase prepared above in (a) was dissolved in 0.15 ml of 0.1M phosphate buffer (pH 6.0). To the solution was added a solution of 1.8 mg of the previously-obtained anti-CEA antibody (Fab′ fragment) in 0.15 ml of 0.1M phosphate buffer (pH 6.0) containing 5 mM sodium ethylenediaminetetraacetate. After 20 hours of reaction at 4° C., the reaction mixture was subjected to gel chromatography using an Ultrogel AcA44-packed column (1.5×45 cm) with 0.1M phosphate buffer (pH 6.5) as the eluent. The eluate fractions were measured for absorbance at 280 nm and enzyme activity. Formation of a peroxidase-rabbit anti-CEA antibody (Fab′ fragment) complex was confirmed in the following manner.

Firstly, the enzyme activity was measured by the method of Gilbert et al. [Analytical Chemistry, 40 (1968), 1256]. Thus, each eluate fraction was diluted 1,800-fold with 0.1 M phosphate buffer (pH 7.0) containing 0.1% bovine serum albumin. To 10 μl of the dilution was added 0.25 ml of 0.5% p-hydroxyphenylacetic acid solution in 0.05M sodium acetate buffer (pH 5.0). After mixing, the mixture was incubated at 30° C. for 5 minutes. Then, to the mixture was added 0.05 ml of 0.01% hydrogen peroxide, and the mixture was reacted at 30° C. for 20 minutes. The enzymatic reaction was terminated by adding 2.5 ml of 0.1M glycine buffer (pH 10.3), and the fluorescence intensity at 405 nm was measured (excitation wavelength 320 nm), the fluorescence intensity due to 1 μg/ml of quinine being taken as 100. The results obtained are given in FIG. 1. In FIG. 1, the data shown by are absorbance (at 280 nm) data and those shown by peroxidase activity (fluorescence intensity) data. The formation of the peroxidase-anti-CEA antibody (Fab′ fragment) complex was found to be very good in fraction 38 and the surrounding fractions.

(6) Production of monoclonal anti-CEA antibody (Fab′)-HRP complex

A 5 mg portion of the monoclonal anti-CEA antibody γ-globulin fraction (Mo-T3) obtained previously in (2) above was dissolved in 1 ml of 0.1M acetate buffer (pH 4.2), followed by addition of 0.25 mg of pepsin. After overnight reaction at 37° C., the mixture was neutralized and applied to a Sephadex G-150 column (2.5 cm in diameter, 55 cm in length) for purification. The F(ab′)₂ fraction obtained was reduced with 2-mercaptoethylamine, and the reduction product was purified by gel chromatography using a Sephadex G-25 column to give monoclonal anti-CEA antibody (Fab′ fragment).

Then, 1.5 mg of the maleimidated peroxidase prepared above in (5)-(a) was dissolved in 0.15 ml of 0.1M phosphate buffer (pH 6.0). A solution of 1.8 mg of the previously-obtained monoclonal anti-CEA antibody (Fab′ fragment) in 0.15 ml of 0.1M phosphate buffer (pH 6.0) containing 5 mM sodium ethylenediaminetetraacetate was added thereto. After overnight reaction at 4° C., the reaction mixture was subjected to gel chromatography using an Ultrogel AcA44-packed column (1.5×45 cm) with 0.05M phosphate buffer (pH 6.5) as the eluent. The eluate fractions were measured for absorbance at 280 nm and enzyme activity in the same manner as in (5) above to collect the desired fractions. The thus-obtained monoclonal anti-CEA antibody (Fab')-HRP complex solution was adjusted to 0.1% BSA and 0.005% merthiolate, and stored at 4° C.

(7) Production of monoclonal anti-CEA antibody (IgG)-HRP complex

To a solution of 5 mg of the monoclonal anti-CEA antibody gamma-globulin fraction (Mo-T2) obtained above in (2) in 1 ml of 0.1M phosphate buffer (pH 6.5), there was added a a solution of 0.22 mg of the coupling reagent MMC (The compound general formula [I], n=1, R=cyclohexylene) in 40 μl of N,N-dimethylformamide. The reaction was carried out at 25° C. with stirring for 45 minutes. The resultant precipitate was removed by centrifugation. The supernatant was applied to a Sephadex G-25 column (1.0×45 cm) and eluted with 0.1 M phosphate buffer (pH 6.8). Protein-containing fractions were collected and concentrated using a collodion membrane. The thus-prepared maleimidated IgG had 5.9 maleimido groups introduced therein per molecule.

Separately, 10 mg of HRP was dissolved in 1.4 ml of 0.1M phosphate buffer (pH 6.5), and a solution of 1.25 mg of the coupling reagent SPDP [N-succinimidyl 3-(2-pyridyldithio)propionate] in 100 μl of ethanol was added, and the reaction was conducted at 25° C. with stirring for 30 minutes. The reaction mixture was applied to a Sephadex G-25 column (1.0×45 cm) and eluted with 0.1M acetate buffer (pH 5.0), to thereby remove SPDP. The eluate was then subjected to reduction by adding 17 mg of dithiothreitol and again to gel chromatography using a Sephadex G-25 (1.0×45 cm) column for purification. Thiolated HRP was thus obtained.

In the next place, 3 mg of the previously-prepared maleimidated IgG concentrated to 0.2 ml was reacted with 6 mg of the thiolated HRP concentrated to 0.2 ml., at 4° C. for 16 hours. Thereafter, the reaction mixture was subjected to gel chromatography using an Ultrogel AcA44 [LKB (France)]-packed column (1.5 cm×45 cm) and 0.1M phosphate buffer (pH 6.5) as the eluent. The eluate fractions were measured for absorbance at 280 nm and enzyme activity in the same manner as in (5) above, and the desired fractions were collected. The thus-obtained monoclonal anti-CEA antibody (IgG)-HRP complex solution was adjusted to 0.1% BSA and 0.005% merthiolate, and stored at 4° C.

(8) Production of monclonal anti-CEA antibody (IgG)-HRP complex

To a solution of 5 mg of the monoclonal anti-CEA antibody gamma-globulin fraction (Mo-T2) obtained above in (2) in 1 ml of 0.1M phosphate buffer (pH 6.5), there was added a solution of 0.6 mg of S-acetylmercaptosuccinic anhydride in 40 μl of N,N-dimethylforamide, and the reaction was carried out at 25° C. for 30 minutes. Then, 0.2 ml of 0.1M Tris buffer (pH 7.0) and 0.2 ml of 1M hydroxylamine were added, and the reaction was continued at 30° C. for further 5 minutes. The reaction mixture was subjected to gel chromatography using a Sephadex G-25 column (1.0×45 cm) for purification, giving thiolated monoclonal anti-CEA antibody (IgG).

Then, 1.5 mg of the maleimidated peroxidase prepared above in (5)-(a) was dissolved in 0.2 ml of 0.1M phosphate buffer (pH 6.0). Thereto was added 0.2 ml of 0.1M phosphate buffer (pH 6.0) containing 3 mg of the previously-obtained thiolated monoclonal anti-CEA antibody (IgG) and 5 mM sodium ethylenediaminetetraacetate, and the reaction was conducted at 4° C. overnight. Thereafter, the reaction mixture was subjected to gel chromatography using an Ultrogel AcA44-packed column (1.5×45 cm) with 0.1M phosphate buffer (pH 6.5) as the eluent. The eluate fractions were measured for absorbance at 280 nm and enzyme activity in the same manner as in (5) above, and the desired fractions were collected. The thus-obtained monoclonal anti-CEA (IgG)-HRP complex solution was adjusted to 0.1% BSA and 0.005% merthiolate, and stored at 4° C.

EXAMPLE 2

(a) Comparison of various HRP complexes (in sensitivity and nonspecific adsorption)

For examining the HRP complexes obtained in Example 1 for performance characteristics, EIA was performed. The following were used as reagents for EIA:

Reagents:

(1) Anti-CEA antibody-sensitized microplate;

(2) HRP complexes obtained in Example 1 and Reference Example 2, and DAKO Immunoglobulins (Denmark) anti-CEA antibody-HRP complex;

(3) Standard CEA;

(4) Buffer B (0.02M phosphate buffer, pH 7.0, containing 10% bovine serum and 0.15M NaCl) and buffer A (0.02M phosphate buffer, pH 7.0, containing 0.15M NaCl);

(5) Reagents necessary for peroxidase activity measurement: 0.1M citric acid-disodium phosphate buffer (pH 4.8) containing 0.02% hydrogen peroxide and 0.15% o-phenylenediamine, and reaction terminator solution (2 N sulfuric acid).

Preparation of antibody-sensitized microplate:

An antibody solution (50 μg/ml) prepared by diluting polyclonal anti-CEA antibody [DAKO Immunoglobulins (Sweden)] with 0.1M carbonate buffer (pH 9.6) was distributed in 100-μl portions into the wells of Immunoplate I for EIA [Nunc (Denmark)] and allowing the plate to stand at 4° C. overnight. The plate was washed with 0.01M phosphate buffer (pH 7.0) containing 0.1% BSA and stored in the cool place until use thereof.

Measurement:

A 100-μl portion of a CEA standard solution in buffer B was poured into each well. After 3 hours of reaction at 37° C., each well was washed with buffer A and, following addition of 100 μl of one of the HRP complexes obtained in Example 1, Reference Example 2 or DAKO Immunoglobulins polyclonal anti-CEA antibody-HRP complex (the enzyme activity being the same, i.e. 30 ng as HRP per well), incubated at 25° C. for 3.5 hours. After washing the well with buffer A, 100 μl of 0.1M citric aciddisodium phosphate buffer (pH 4.8) containing 0.02% hydrogen peroxide and 0.15% o-phenylenediamine was added to the well. After 30 minutes of incubation at 30° C., the reaction was terminated by adding 100 μl of 2 N sulfuric acid to each well, and the absorbance at 490 nm was measured, with the blank as a control, using an automatic colorimeter for microplates [Titertek Multiskan, Flow (U.S.A.)]. The results thus obtained are shown in Table 2. The HRP complexes according to the invention as obtained in Example 1 each showed a very low level of nonspecific adsorption on the well and gave a high level of sensitivity, as compared with the HRP complex obtained in Reference Example 2 and DAKO Immunoglobulins HRP complex [two step glutaraldehyde method; Immunochemistry, 8 (1971), p.1175].

TABLE 2

| Anti-CEA antibody-HRP complex | Absorbance at 490 nm CEA (ng/ml) | | | |
|---|---|---|---|---|
| | 0 | 0.3 | 1.0 | 3.0 |
| Example 1 (5) | 0.005 | 0.150 | 0.410 | 1.354 |
| Example 1 (6) | 0.002 | 0.122 | 0.444 | 1.332 |
| Example 1 (7) | 0.002 | 0.175 | 0.500 | 1.462 |
| Example 1 (8) | 0.006 | 0.130 | 0.402 | 1.173 |
| Reference Example 2 | 0.055 | 0.123 | 0.395 | 0.930 |
| one manufactured by DAKO immunoglobulins | 0.045 | 0.070 | 0.120 | 0.253 |

(b) Immunochemical assay kit for CEA and assay of CEA

Using the immunochemical CEA assay kit described below and following the procedure mentioned below, serum CEA concentrations in normal humans and in cancer-bearing patients were measured:

Immunochemical assay kit for CEA:

(1) Antibody-sensitized polystyrene beads prepared by immersing 1,500 polystyrene beads (4.8 mm in diameter; Precision Plastics Ball Co., Chicago, U.S.A.) in 100 ml of 15 μg/ml solution of the monoclonal anti-CEA antibody gammaglobulin fraction (Mo-T4) obtained in Example 1-(2) in 0.01 M NaCl-0.01M phosphate buffer (pH 8.0), followed by overnight incubation at 5° C. and washing with 0.05M phosphate buffer (pH 7.0) containing 0.1% BSA;

(2) Peroxidase-labelled anti-CEA antibody complex obtained in Example 1-(7);

(3) 0 to 200 ng of standard CEA;

(4) Buffer A and Buffer B (see the preceding paragraph (a)) for use in diluting the above reagent (3) and the test samples;

(5) o-Phenylenediamine;

(6) Buffer C for use in diluting the above reagent (2); 0.1M phosphate buffer, pH 7.5, containing 0.1% bovine serum albumin and 0.002% merthiolate;

(7) Buffer D for use in diluting the above reagent (5); 0.1M citrate buffer, pH 4.8, containing 0.02% hydrogen peroxide and 0.002% merthiolate;

(8) Terminator solution; 2 N sulfuric acid.

Procedure:

To 50 μl of standard CEA solution or test sample, add 250 μl of reagent (4) buffer B and one piece of reagent (1). Allow the reaction to proceed at room temperatue for 1 day. Wash the polystyrene bead with buffer A, and add 300 μl of a dilution of reagent (2) (about 30 ng as complex) diluted with reagent (6). Allow the reaction to progress at 4° C. for 1 day. Wash the polystyrene bead with buffer A, and add 500 μl of 0.15% solution of reagent (5) in reagent (7). Allow the reaction to proceed at room temperature for 40 minutes. Terminate the reaction by adding 1.5 ml of 2 N sulfuric acid. Measure the absorbance at 492 nm.

Serum CEA concentrations in normal humans and in cancer-bearing patients were measured by the above method. The results obtained are shown in Table 3.

TABLE 3

| Test sample | CEA level (ng/ml) |
|---|---|
| Normal subject, serum 1 | 0.5 |
| Normal subject, serum 2 | 1.0 |
| Normal subject, serum 3 | 0.7 |
| Normal subject, serum 4 | 1.6 |

TABLE 3-continued

| Test sample | CEA level (ng/ml) |
|---|---|
| Normal subject, serum 5 | 1.2 |
| Patients with gallbladder cancer | |
| Serum 1 | 8.7 |
| Serum 2 | 10.3 |
| Patients with liver cancer | |
| Serum 1 | 6.4 |
| Serum 2 | 20.8 |
| Patients with stomach cancer | |
| Serum 1 | 1.4 |
| Serum 2 | 9.6 |
| Serum 3 | 5.0 |
| Patients with colon cancer | |
| Serum 1 | 565 |
| Serum 2 | 38.5 |
| Serum 3 | 113 |
| Patient with spleen cancer | |
| Serum 1 | 5.7 |

The assay results indicated that the CEA level in normal human serum varied within the range of 0.5 to 1.2 ng/ml (mean=1.0 ng/ml), and the CEA values for various cancer patients were higher, with a maximum value of 565 ng/ml.

EXAMPLE 3

Immunochemical assay kit for CEA:

Using the immunochemical CEA assay kit described below and following the procedure mentioned below.

Immunochemical assay kit for CEA:

Reagents:

(1) Anti-CEA antibody-sensitized microplate;

(2) Peroxidase-labelled anti-CEA antibody complex obtained in Example 1-(8);

(3) Standard CEA;

(4) Buffer B (0.02M phosphate buffer, pH 7.0, containing 10% bovine serum and 0.15M NaCl) and buffer A (0.02M phosphate buffer, pH 7.0, containing 0.15M NaCl);

(5) Reagents necessary for peroxidase activity measurement: 0.1M citric acid-disodium phosphate buffer (pH 4.8) containing 0.02% hydrogen peroxide and 0.15% o-phenylenediamine, and reaction terminator solution (2 N sulfuric acid).

Preparation of antibody-sensitized microplate:

An antibody solution (50 μg/ml) prepared by diluting the monoclonal anti-CEA antibody gamma-globulin fraction (Mo-K5) with 0.1M carbonate buffer (pH 0.6) is distributed in 100-μl portions into the wells of Immunoplate I for EIA [Nunc (Denmark)] and allowing the plate to stand at 4° C. overnight. The plate is washed with 0.01M phosphate buffer (pH 7.0) containing 0.1% BSA and stored in the cool place until use thereof.

Measurement:

A 100-μl portion of a CEA standard solution in buffer B is poured into each well. After 3 hours of reaction at 37° C., each well is washed with buffer A and, following addition of 100 μl of one of the peroxidase-labelled anti-CEA antibody complex obtained in Example 1-(8), incubated at 25° C. for 3.5 hours. After washing the well with buffer A, 100 μl of 0.1M citric acid-disodium phosphate buffer (pH 4.8) containing 0.02% hydrogen peroxide and 0.15% o-phenylenediamine is added to the well. After 30 minutes of incubation at 30° C., the reaction is terminated by adding 100 μl of 2 N sulfuric acid to each well, and the absorbance at 490 nm is measured, with the blank as a control, using an automatic colorimeter for microplates [Titertek Multiskan, Flow (U.S.A.)].

EXAMPLE 4

Immunochemical assay kit for CEA and assay of CEA:

Using the immunochemical CEA assay kit described below and following thepprocedure mentioned below, serum CEA concentrations in normal humans and in cancer-bearing patients were measured:

Immunochemical assay kit for CEA:

Reagents:

(1) Anti-CEA antibody-sensitized microplate;

(2) Peroxidase-labelled anti-CEA antibody complex obtained in Example 1-(7);

(3) Standard CEA;

(4) Buffer B (0.02M phosphate buffer, pH 7.0, containing 10% bovine serum and 0.15M NaCl) and buffer A (0.02M phosphate buffer, pH 7.0, containing 0.15M NaCl);

(5) Reagents necessary for peroxidase activity measurement: 0.1M citric acid-disodium phosphate buffer (pH 4.8) containing 0.02% hydrogen peroxide and 0.15% o-phenylenediamine, and reaction terminator solution (2 N sulfuric acid).

Preparation of antibody-sensitized microplate:

An antibody solution (50 μg/ml) prepared by diluting the monoclonal anti-CEA antibody gamma-globulin fraction (MO-K5) obtained in reference Example 1-(2) with 0.1M carbonate buffer (pH 9.6) was distributed in 100 μl portions into the wells of Immunoplate I for EIA [Nunc (Denmark)] and allowing the plate to stand at 4° C. overnight. The plate was washed with 0.01M phosphate buffer (pH 7.0) containing 0.1% BSA and stored in the cool place until use thereof.

Measurement:

A 100 μl portion of a CEA standard solution in buffer B was poured into each well. After 3 hours of reaction at 37° C., each well was washed with buffer A and, following addition of 100 μl of one of the peroxidase-labelled anti-CEA antibody complex obtained in Example 1-(7), incubated at 25° C. for 3.5 hours. After washing the well with buffer A, 100 μl of 0.1M citric acid-disodium phosphate buffer (pH 4.8) containing 0.02% hydrogen peroxide and 0.15% o-phenylenediamine was added to the well. After 30 mintes of incubation at 30° C., the reaction was terminated by adding 100 μl of 2 N sulfuric acid to each well, and the absorbance at 490 nm was measured, with the blank as a control, using an automatic colorimeter for microplates [Titertek Multiskan, Flow (U.S.A.)]. The results thus obtained are shown in Table 4.

TABLE 4

| Test sample | CEA level (ng/ml) |
| --- | --- |
| Normal subjects | |
| serum A | 1.6 |
| B | 1.5 |
| C | 1.5 |
| D | 1.0 |
| Patients with colorectal carcinoma | |
| serum A | 131.0 |
| B | 14.0 |
| C | 13.8 |
| D | 88.0 |
| E | 8.4 |
| F | 12.0 |

EXAMPLE 5

Immunochemical assay kit for CEA

Using the immunochemical CEA assay kit described below and following the procedure mentioned below.

Immunochemical assay kit for CEA:

(1) Antibody-sensitized polystyrene beads prepared by immersing 1,500 polystyrene beads (4.8 mm in diameter; Precision Plastics Ball Co., Chicago, U.S.A.) in 100 ml of 15 μg/ml solution of the monoclonal anti-CEA antibody gammaglobulin fraction (Mo-K5) obtained in Reference Example 1-(2 in 0.01M NaCl-0.01M phosphate buffer (pH 8.0), followed by overnight incubation at 5° C. and washing with 0.05M phosphate buffer (pH 7.0) containing 0.1% BSA;

(2) Peroxidase-labelled anti-CEA antibody complex obtained in Example 1-(7);

(3) 0 to 200 ng of standard CEA;

(4) Buffer A (0.02M phosphate buffer, pH 7.0, containing 0.15M Nacl) and Buffer B (0.02M phosphate buffer, pH 7.0, containing 10% bovine serum and 0.15M NaCl) for use in diluting the bove reagent (3) and the test samples;

(5) o-phenylenediamine;

(6) Buffer C for use in diluting the above reagent (2); 0.1M phosphate buffer, pH 7.5, containing 0.1% bovine serum albumin and 0.002% merthiolate;

(7) Buffer D for use in diluting the above reagent (5); 0.1M citrate buffer, pH 4.8, containing 0.02% hydrogen peroxide and 0.002% merthiolate;

(8) Terminator solution; 2 N sulfuric acid.

Procedure:

To 50 μl of standard CEA solution or test sample, is added 250 μl of reagent (4) buffer B and one piece of reagent (1). The reaction is allowed to proceed at room temperature for 1 day. The polystyrene bead is washed with buffer A, and is added 300 μl of a dilution of reagent (2) (about 30 ng as complex) diluted with reagent (6). The reaction is allowed to progress at 4° C. for 1 day. The polystyrene bead is washed with buffer A, and add 500 μl of 0.15% solution of reagent (5) in reagent (7). The reaction is allowed to proceed at room temperature for 40 minutes. The reaction is terminated by adding 1.5 ml of 2 N sulfuric acid, and then the absorbance is measured at 492 nm.

What we claim is:

1. In an immunochemical assay method for human carcinoembryonic antigen, which comprises adding a test sample to a first antibody reactive to human carcinoembryonic antigen supported on a carrier, adding a second antibody reactive to human carcinoembryonic antigen labelled with a labelling agent to the resultant mixture, and determining enzymatic activity of the resultant product, an improvement which comprises that (1) one of said first and second antibodies is specifically reactive to human carcinoembryonic antigen and the other is reactive to a human non-specific cross reacting antigen, (2) at least one of said first and second antibodies is a monoclonal antibody, (3) said labelling agent is peroxidase, and (4) said peroxidase is coupled with said second antibody by means of a coupling compound of the formula:

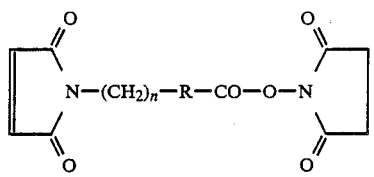

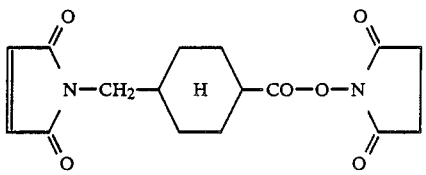

wherein n is an integer of 0 to 5 and R is a chemical bond or a divalent 6-membered cyclic hydrocarbon residue.

2. A method as claimed in claim 1, wherein the first antibody is a monoclonal or polyclonal antibody and is reactive to a human non-specific cross reacting antigen, and the second antibody is a monoclonal antibody and is specifically reactive to human carcinoembryonic antigen.

3. A method as claimed in claim 2, wherein the first antibody is a monoclonal antibody.

4. A method as claimed in claim 1, wherein the first and second antibodies are IgG or F(ab')$_2$ fractions.

5. A method as claimed in claim 1, wherein the peroxidase is horseraddish peroxidase.

6. A method as claimed in claim 1, wherein the peroxidase has a thiol group.

7. A method as claimed in claim 6, wherein the peroxidase is bound through a sulfur atom to the maleimide moiety of the coupling compound, and the second antibody is bound through an amino group thereof to the carbonyl moiety of the coupling compound by removal of the succinimide ether moiety from the coupling compound.

8. A method as claimed in claim 1, wherein the coupling compound is a compound of the formula:

9. A method as claimed in claim 1, wherein the human non-specific cross reacting antigen is NCA-2.

10. In a packaged set for immunochemical assay of human carcinoembryonic antigen, which comprises a first antibody reactive to human carcinoembryonic antigen supported on a carrier, and a second antibody reactive to human carcinoembryonic antigen labelled with a labelling agent, an improvement which comprises that (1) one of said first and second antibodies is specifically reactive to human carcinoembryonic antigen and the other is a human non-specific cross reacting antigen, (2) at least one of said first and second antibodies is a monoclonal antibody, (3) said labelling agent is peroxidase, and (4) said peroxidase is coupled with said second antibody by means of a coupling compound of the formula:

wherein n is an integer of 0 to 5 and R is a chemical bond or a divalent 6-membered cyclic hydrocarbon residue.

* * * * *